United States Patent [19]

Ieoka

[11] Patent Number: 4,878,112
[45] Date of Patent: Oct. 31, 1989

[54] ELECTRONIC TYPE ENDOSCOPE APPARATUS FOR USE IN NTSC/PAL SYSTEMS

[75] Inventor: Shoichi Ieoka, Hachioji, Japan
[73] Assignee: Olympus Optical Co., Ltd., Tokyo, Japan
[21] Appl. No.: 224,527
[22] Filed: Jul. 26, 1988

[30] Foreign Application Priority Data
Jul. 27, 1987 [JP] Japan .................... 62-188604

[51] Int. Cl.⁴ .................... H04N 7/18; G61B 1/4
[52] U.S. Cl. .................... 358/98; 358/42; 128/6
[58] Field of Search .................... 358/98, 42; 128/4, 6

[56] References Cited

U.S. PATENT DOCUMENTS 4,628,350 12/1986 Aughton et al. .................... 358/42 X
4,800,424 1/1989 Noguchi .................... 358/98

FOREIGN PATENT DOCUMENTS 60-73613 4/1985 Japan .

Primary Examiner—James J. Groody
Assistant Examiner—Victor R. Kostak
Attorney, Agent, or Firm—Armstrong, Nikaido, Marmelstein, Kubovick & Murray

[57] ABSTRACT

A rotary color filter, used in a PAL or NTSC system, is rotated with a period which is equal to one frame period of a video signal. The rotary color filter has a plurality of color transmitting filters which are disposed in the circumferential direction at different intervals. Consequently the time during which an illumination light is emitted to obtain one complete color frame is made shorter, thereby diminishing the possibility of a color change occurring.

17 Claims, 6 Drawing Sheets

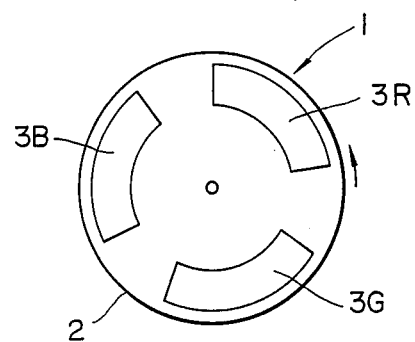
FIG.1 *(PRIOR ART)*
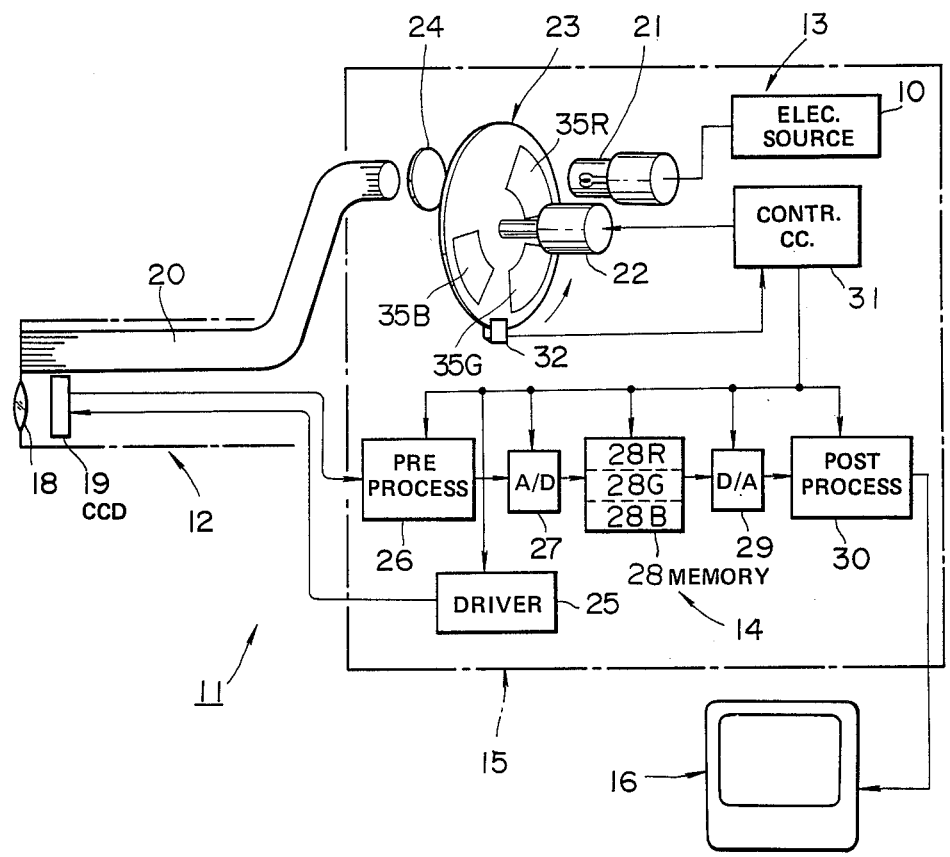
FIG.2

ELECTRONIC TYPE ENDOSCOPE APPARATUS FOR USE IN NTSC/PAL SYSTEMS

BACKGROUND OF THE INVENTION

1. Field of the Invention

The present invention relates to an electronic type endoscope apparatus for use in the NTSC/PAL systems which can readily cope with video systems having different frame periods.

2. Description of the Prior Art

In recent years, endoscopes have been widely employed which enable an object portion, located deep inside a body cavity, to be observed without requiring a discission by inserting an elongate insertable portion in the body cavity. The endoscopes also enable treatment with instruments, if necessary.

Also, electronic type endoscopes (also called electronic endoscopes or electronic scopes) have recently been put into practical use which do not use an image guide formed by an optical fiber bundle (this type of endoscope is called an optical fiber bundle), and in which an image is converted into electric signals by a solid state imaging element such as a charge coupled device. Picture signals which have been transmitted through a signal cable are displayed on a monitor.

Electronic type endoscopes fall into two categories: a color mosaic type in which a mosaic color filter array is disposed in front of the solid state imaging element so as to obtain a color image of an object which has been illuminated by white light, and a field sequential type in which images obtained by a monochrome solid state imaging element by sequentially illuminating an object by a light having various wavelengths in, for example, the red, green, and blue ranges are superimposed on top of one another to obtain a color image.

The aforementioned field sequential color imaging system uses a rotary color filter 1 such as that shown in FIG. 1 if it is of the type which is used in the NTSC or PAL system.

The rotary color filter 1 has a disk-shaped light shielding plate 2. The light shielding plate 2 has three fan-shaped openings for the purpose of providing a light of three colors. The openings are provided with a red light transmitting filter 3R, a green light transmitting filter 3G, and a blue light transmitting filter 3B, respectively. A portion adjacent to filter 3I (I represents R, G or B) forms a light shielding portion which provides a read-out of signals from an imaging element or a transfer of signals therein. the ratio of the opening for the filter 3I to the light shielding portion is determined so that a) the width of the light shielding portion is set to a minimum value that is required for read out or transfer of signals and b) the width of the opening is set to a maximum value which ensures the white balance of a light comprising the three colors.

In order to display the picture signals output from the imaging element on the TV monitor, the rotary color filter 1 is rotated at a speed which corresponds to a frame repetition rate of 30 frames/second in the NTSC system and at a speed corresponding to a frame repetition rate of 25 frames/second in the PAL system so that the rotation speed is synchronized with TV synchronizing signals, where the same rotary color filter 1 can be used in the both systems. In other words, the rotary color filter 1 is rotated at a speed of 30 turns/second in the NTSC system and 25 turns/second in the PAL system.

In a case where the above-described conventional rotary color filter is employed, the opening time (illuminating time) is longer in the PAL system than that in the NTSC system, which ensures bright illumination. However, color change, which is characteristic of the field sequential method, is more likely to occur in the PAL system than in the NTSC system.

Japanese Patent Laid-Open No. 60-73613 discloses a rotary filter having variable light-shielding plates that can adjust the openings to a suitable value. However, this is not designed to diminish the color change.

SUMMARY OF THE INVENTION

An object of the present invention is to provide an electronic type endoscope apparatus which can readily cope with both the NTSC and PAL systems, and which enables color change to be diminished in the PAL system.

Another object of the present invention is to provide an electronic type endoscope apparatus which ensures the same characteristics when the apparatus is applied to systems such as the NTSC and PAL systems having different frame periods.

Another object of the present invention is to provide an electronic type endoscope apparatus which enables a large number of components to be used in common when the apparatus is applied to systems which have different frame periods.

To this end, the present invention provides an electronic type endoscope apparatus in which a rotary color filter is rotated with a period which is equal to the frame period of a predetermined video signal therefor. A plurality of color transmitting filters are disposed at unequal intervals in the circumferential direction so as to shorten the period needed to obtain one color frame, thereby diminishing color change, and enabling the same characteristics to be obtained as those in other video systems having a shorter frame period.

BRIEF DESCRIPTION OF THE DRAWINGS

FIG. 1 is a front view of a known rotary color filter for use in the PAL system;

FIG. 2 is a view of an electronic type endoscope apparatus, showing a first embodiment of the present invention;

DESCRIPTION OF THE PREFERRED EMBODIMENTS

Figure 3:
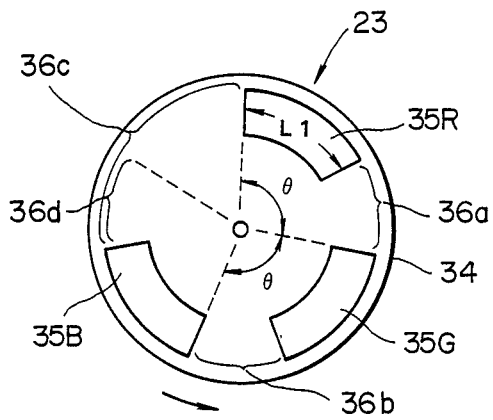
FIG. 3 is a front view of a rotary color filter for use in the PAL system which is used in the endoscope apparatus of FIG. 2.

A first embodiment of the present invention will be described below with reference to FIGS. 2 to 7. Referring first to FIG. 2, an electronic type endoscope apparatus 11 includes an electronic scope 12. A video processor 15 is connected to the electronic scope 12 and incorporates a light source device 13, for supplying illumination light, and a signal processing circuit 14. A color TV monitor 16 is connected to the output terminal of the signal processing circuit 14 for displaying an endoscope image.

The electronic scope 12 has an insertable portion which is flexible and long enough to be inserted into a body cavity. The forward end of the insertable portion incorporates an imaging means which includes an objective lens 18 and a solid state imaging element, such as a CCD, disposed in the focal plane of the objective lens 18.

The insertable portion contains a light guide 20 formed of a bundle of flexible fibers which transmits light. The light is supplied from the light source device 13 by mounting a light guide connector provided on the light incident end of the light guide 20 on the video processor 15. The light source device 13 includes a light source lamp 21, a rotary color filter 23 disposed in the optical path of the light emitted from the light source lamp 21. The rotary color filter 23 is rotated by a motor 22. A condenser lens 24 condenses the light of red, green, and blue colors which has passed through the rotary color filter 23 onto the light guide connector. A power source 10 supplies power to light the lamp 21.

The images of an object sequentially illuminated by light of red, green, and blue colors are formed by the objective lens 18 on an image area of the CCD 19 where they are photoelectrically converted. The converted signals are read out from the CCD 19 to a preprocessing circuit 26 by the application of a drive signal from a driver 25. After having been correlation sampled or gamma corrected by the preprocessing circuit 26, the signals are input to an A/D converter 27 where they are converted into digital signals. The digital signals are then input to a frame memory 28. In the frame memory 28, the image data obtained from the red, green, and blue light is sequentially stored in three memories 28R, 28G, and 28G which form the frame memory 28. The image data obtained from the red, green, and blue light, which has been stored in the memory 28, is read out from the memory 28 at the same time to a D/A converter 29 where the image data is converted into analog signals. The analog signals are input to a postprocessing circuit 30 where they are converted into a composite video signal for use in the PAL system. The video signal is then input to the color TV monitor 16 which uses the PAL system so that the video signal is color displayed thereon.

As shown in FIG. 2, a control circuit 31, incorporating a reference generator, controls the timing of the driver 25, the preprocessing circuit 26, the A/D converter 27, the memory 28, the D/A converter 29, and the postprocessing circuit 30. Also, the control circuit 31 receives a signal representing the rotational speed of the rotary filter 23 from a rotational speed detecting sensor 32 for detecting the rotational speed of the rotary filter 23 (which may be a photo interrupter or a photo reflector), and thereby controls the rotational speed of the motor 22 so that the motor is synchronized with the reference clock.

If the rotational speed detecting sensor 32 is a photo interrupter, the periphery of the rotary color filter 23 that faces the photo interrupter is provided with a small hole (not shown).

The rotational speed detecting means may also comprise a rotary encoder mounted on the rotary shaft of the motor 22.

In the rotary color filter 23 used in the first embodiment, a light shielding disk-shaped frame 34 has three fan-shaped openings in the circumferential direction, as shown in FIG. 3. A red light transmitting filter 35R, a green light transmitting filter 35G, and a blue light transmitting filter 35B are respectively mounted over these three openings. However, the filters 35R, 35G, and 35B are not disposed equiangularly, unlike the known rotary color filter shown in FIG. 1 (in which the angles formed in the rotational direction between the starting ends of adjacent filters are all about 120 degrees). More specifically, the red light transmitting filter and the green light transmitting filter are disposed on the disk-shaped frame 34 such that the angle formed between the starting end of the filter 35R and that of the filter 35B and the angle formed between the starting end of the filter 35G and that of the filter 35B are respectively θ, which is less than 120 degrees, while the angle formed between the starting end of the filter 35B and that of the filter 35R is larger than the other two angles. The same thing applies to light shielding portions 36a, 36b, and 36c formed between adjacent filters. More specifically, the light shielding portion 36a formed between the red light transmitting filter 35R and the green light transmitting filter 35G is made equal to the light shielding portion 36b formed between the green light transmitting filter 35G and the blue light transmitting filter 35B, whereas the light shieling portion 36c formed between the blue light transmitting filter 35B and the red light transmitting filter 35R is made larger than the other two light shielding portions.

The rotary color filter 23 is rotated by the motor 22 in the direction indicated by the arrow at a constant speed. At this time, the filters 35R, 35G, and 35B are placed in the optical path for periods of time which are shown as the periods of illumination in FIG. 4 (a) or as the exposure periods in FIG. 4 (b) (Illumination with red light that has passed through the red light transmitting filter 35R is shown as R light, and the period for the R light is the period of illumination with red light. Since the CCD 19 is exposed to this R light, the period during which the CCD 19 is exposed to it is denoted by R exposure. The same thing applies to G light and B light.). The periods during which the light shielding portions 36a, 36b, and 36c are placed in the optical path represent read out periods. Within the period during which the light shielding portion 36c is put in place, dark current which has been accumulated in the CCD 19 is removed in a light shielding period T2 which follows a normal read out period T1 corresponding to a light shielding portion 36d which is equal to the light shielding portion 36a or 36b.

More specifically, signals are normally read out from the CCD 19 by the application thereto of vertical transfer clocks $\phi v$ and horizontal transfer clocks $\phi h$ by the driver 25, the horizontal transfer clocks $\phi h$ for one horizontal line of pixels being applied subsequent to each vertical transfer clock.

Figure 5:
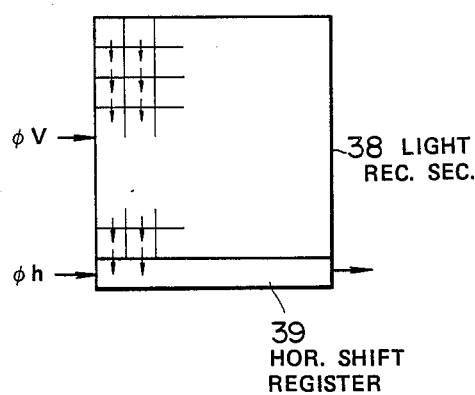
FIG. 5 is a schematic view of a solid state imaging element.
Figure 6:
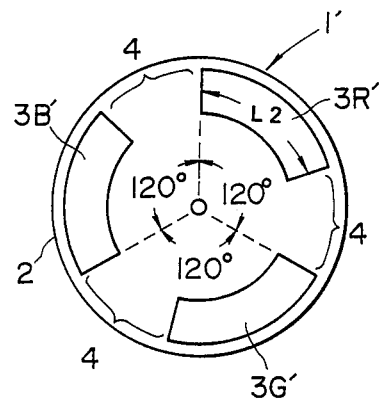
FIG. 6 is a front view of a rotary color filter for use in the NTSC system.

The CCD 19 is of a line transfer type, and therefore includes a light receiving section 38, and a horizontal shift register 39, as shown in FIG. 5. The light receiving section 38 has the functions of (a) storing photoelectrically converted charges for each pixel and of (b) transferring information stored in each horizontal line of pixels vertically (toward the horizontal shift register 39) by the application of a vertical transfer clock $\phi v$.

This means that the information stored in the lowermost line of pixels is transferred to the horizontal shift register 39 by the application of one vertical transfer clock $\phi v$, and that it is read out from the horizontal shift register 39 in synchronism with the clocks $\phi h$ by the application of horizontal transfer clocks $\phi h$ following the application of the vertical transfer clock $\phi v$. Next, the information stored in the second lowest line of pixels is transferred to the horizontal shift register 39 by the application of the second vertical transfer clock $\phi v$, and is then read out from the horizontal shift register 39 in the same manner. The picture signal output from the horizontal shift register 39 is input to the preprocessing circuit 26.

During elimination of dark current, vertical transfer clocks $\phi v$ are applied to the CCD 19, as shown in FIG. 4d, whereas no horizontal transfer clock $\phi h$ is applied at this time, as shown in FIG. 4c. However, a horizontal transfer clock $\phi h$ is applied to the horizontal shift register 39 to enable elimination of dark current to be started immediately before the period of the light shielding, provided by the light shielding portion 36c has ended. However, if the horizontal shift register 39 is of the type which can be reset by the application of a reset signal, a reset signal may be applied thereto in place of the horizontal transfer clock $\phi h$.

The vertical transfer clocks $\phi v$ used to eliminate dark current are applied at intervals which are shorter than when they are applied during normal read out and the number thereof is, at the minimum, equal to the number of vertical lines.

Since dark current generally occurs at a low level, the possibility that the charges will overflow, where the charges are sequentially added in the horizontal shift register 39 as a result of the application of vertical transfer clocks $\phi v$, is very low even when no horizontal transfer clocks $\phi h$ are applied. However, if there is a risk of overflow, horizontal transfer clocks $\phi h$ may be interposed.

Although the rotary color filter 23 is rotated by the motor 22 at a speed of 25 revolutions/second, the period needed to provide one complete color frame Tc (which corresponds to that needed to scan the picture in order to obtain three frames each in a different color) excluding the elimination period is set to 1/30 second, which is the frame repetition rate of the NTSC system.

Figure 4:
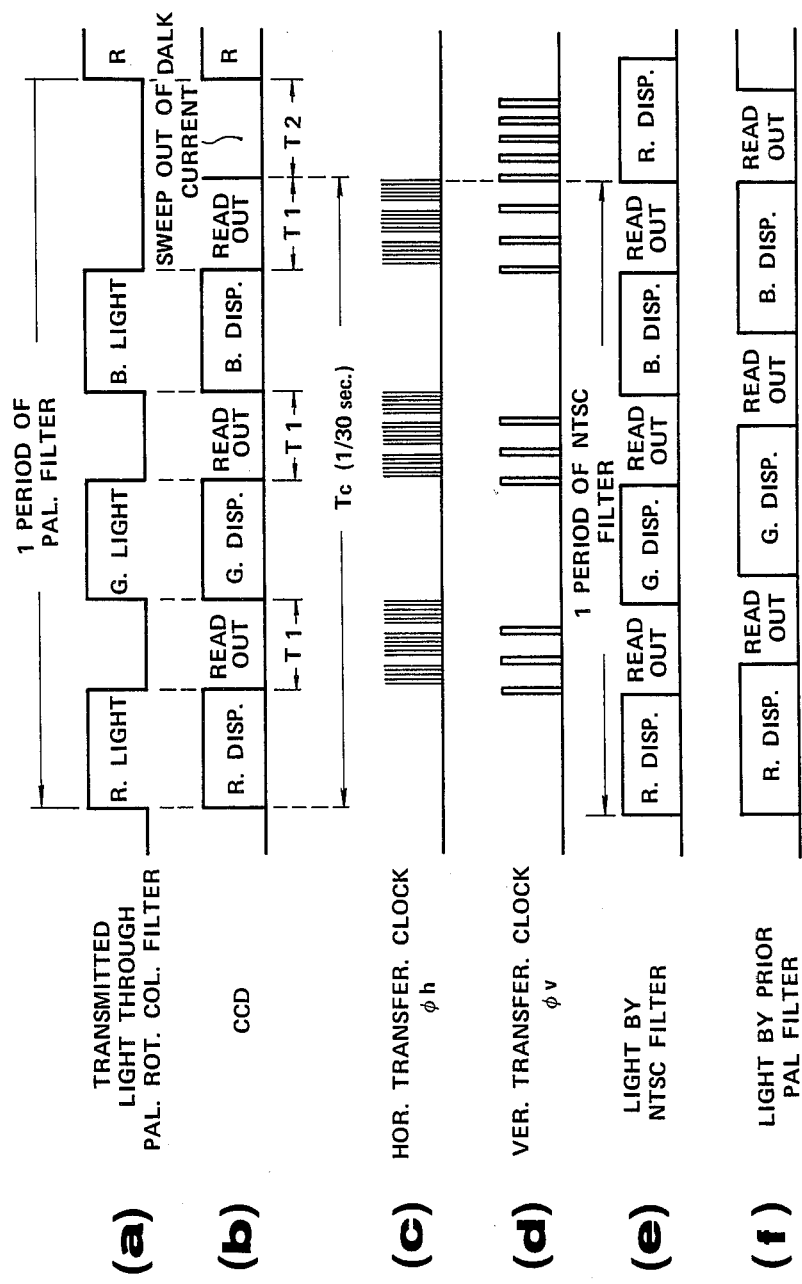
FIG. 4 illustrates the operation of the first embodiment.
Figure 7:
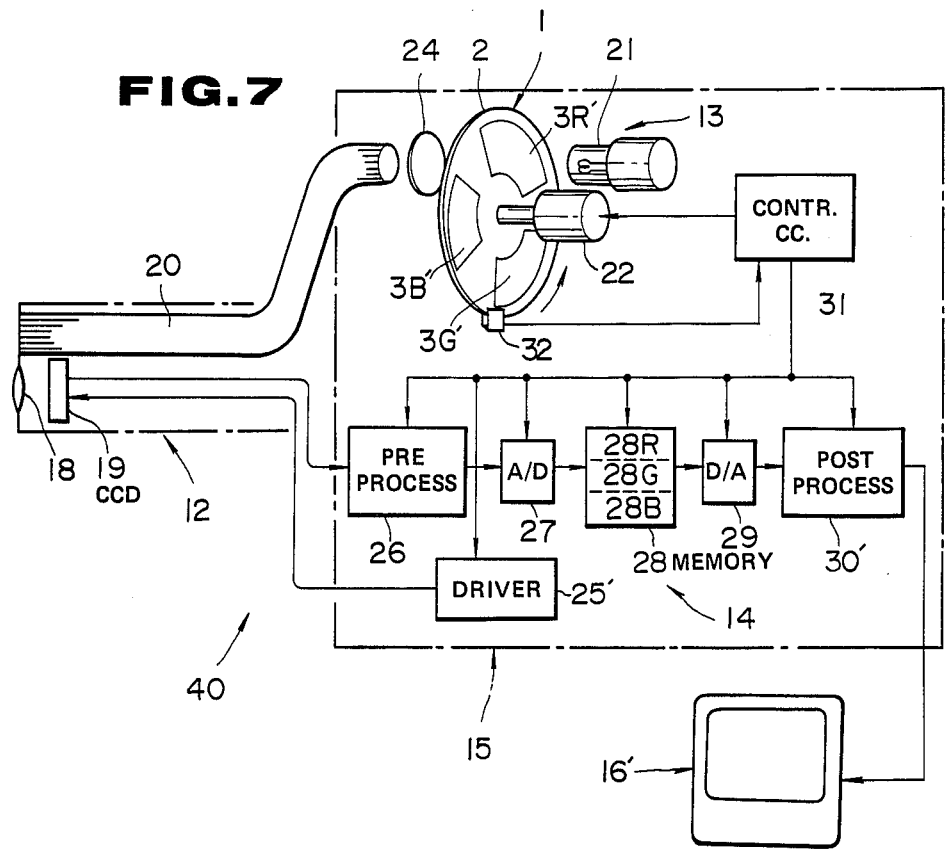
FIG. 7 is a view of an electronic type endoscope apparatus for use in the NTSC system.

If the NTSC system is used for the color monitor which displays an endoscope image, a rotary color filter 1' (shown in FIG. 6) having the same structure as that shown in FIG. 1 is used, and this is operated with respect to the CCD 19 in the manner shown in FIG. 4 (e). For comparison, the operation of the known rotary color filter 1 for use in the PAL system (shown in FIG. 1) is illustrated in FIG. 4 (f). As can be seen from the graph, the rotary color filter 1 is rotated at a speed of 25 turns/second, but no elimination of dark current is performed.

Thus, the first embodiment uses a rotary color filter on which the three filters 35R, 35G, and 35B are disposed in the circumferential direction at different intervals. Consequently, the period needed to provide one complete color frame can be shorter than that needed when the known rotary color filter 1 for use in the PAL system is used, and the occurrence of a color change is therefore restricted. More specifically, one complete color picture can be obtained in a time period which is shorter than that needed when the known rotary color filter 1 for the PAL system is used for a time period equal to the sweep out or elimination period shown in FIG. 4 (b), and the possibility of a color change occurring is therefore reduced. Further, since the one complete color frame period Tc is set to 1/30 second which is the frame repetition rate of the NTSC system, if the NTSC system is used for the color monitor, a large number of common components may be used to process signals by using the rotary color filter 1' shown in FIG. 6. In other words, if the electronic type endoscope of this embodiment is used in the NTSC system, it may be used as an electronic type endoscope 40 for use in the NTSC system shown in FIG. 7. This differs from the electronic type endoscope shown in FIG. 2 only in that the rotary color filter 23, the driver 25, the postprocessing circuit 30, and the color monitor 16 are respectively replaced by the rotary color filter 1' shown in FIG. 6, a driver 25' which does not conduct sweep out operations, a postprocessing circuit 30' for use in the NTSC system, and a color monitor 16' for use in the NTSC system.

The rotary color filter 1' has three color light transmitting filters 3R', 3G', and 3B' which are mounted on a light shielding disk 2' equiangularly. That is, the filters are mounted on the disk 2' in such a manner that the angle formed by the starting end of one filter and that of a subsequent filter in the circumerential direction is 120 degrees. A light shielding portion 4 is provided between adjacent color light transmitting filters 3R' and 3G', 3G' and 3B', or 3B' or 3R'. Read out of signals from the CCD is performed during the time each light shielding portion 4 is positioned in the optical path. This is illustrated in Fig. 4 (e). As is clear from the figure, no sweep out is performed when the NTSC filter 1' is employed.

Although the time required for the PAL rotary filter 23 and the NTSC rotary filter 1' to be turned one revolution is 1/25s and 1/30s, respectively, the illumination periods (exposure periods) and the read out periods for R light, G light, and B light in the PAL system are respectively made to be equal to those in the NTSC system, as will be seen from FIGS. 4 (a) and 4 (e). In order to achieve this, the circumferential lengths L1 nd L2 of the color transmitting filters 35R and 3R' of the filters 23 and 1' are set to values expressed by an equation of $L1 = (5/6) \times L2$. Further, the circumferential length of the light shielding portion 36c of the PAL rotary filter is made longer than that of the light shielding portion 36a or 36b by a value corresponding to 60 degrees (or a value corresponding to (1/25−1/30) second, if the filter is rotated with a period of 1/25s). Consequently, a large number of common components can be used to process signals when the PAL color monitor 16 and the NTSC color monitor 16' are used in the endoscope apparatus, reducing the production cost. Further, products having uniform quality and characteristics can be manufactured for both systems. If the signal level of the dark current is so low as to be neglected, elimination of the dark current may not be necessary. This further simplifies the structure of the signal processing circuit (for example, the driver circuits 25 and 25' may be made the same).

Figure 8:
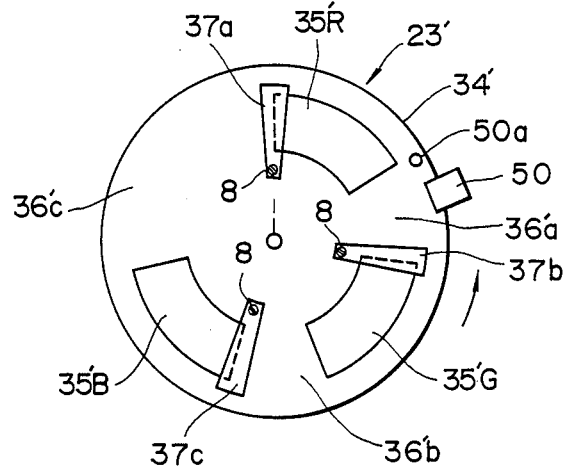
FIG. 8 is a front view of a rotary color filter for use in the PAL system, showing a second embodiment of the present invention.

A second embodiment of the present invention will be described below with reference to FIG. 8 which shows a PAL rotary color filter 23'.

In this rotary color filter 23', the length (that in the circumferential direction) of three color light transmitting filters 35'R, 35'G, and 35'B can be adjusted by light shielding pieces 37a, 37b, 37c that are movable in the circumferential direction, respectively.

Each light shielding piece 37i (i represents a, b, and c) is movable in the circumferential direction along a guide groove provided on a light shielding disk 34'. It can also be fixed at an adjusted position by a screw 8.

The light shielding piece 37i is provided at the forward end of the color light transmitting filter 35'I (I represents R, G, and B) with respect to the rotational direction of the rotary filter, and the rear end of the filter 35'I is fixed no matter where the light shielding piece 37i is positioned. In the vicinity of the rear end of the red light transmitting filter 35'R is provided a small hole 50a which serves as a mark used when read-out timing is detected by a position sensor 50. The position sensor 50 may be a photo interrupter which includes a light-emitting element and a light-receiving element disposed in such a manner as to face each other with the peripheral portion of the disk 34' therebetween.

The length of light shielding portions 36'a and 36'b is set to a value large enough to ensure that all the pixels in the CCD are read out. While a light shielding portion 36'c is positioned in the optical path, elimination of dark current is performed in addition to the normal read-out of signals.

In the second embodiment, white balance control can be done by the light shielding piece 37i.

In other words, when the endoscope image of a white object is to be displayed on the color monitor 16, the white in the object does not appear white on the display. In that case, control of the white balance can be performed by adjusting the light shielding piece 37i.

Figure 9:
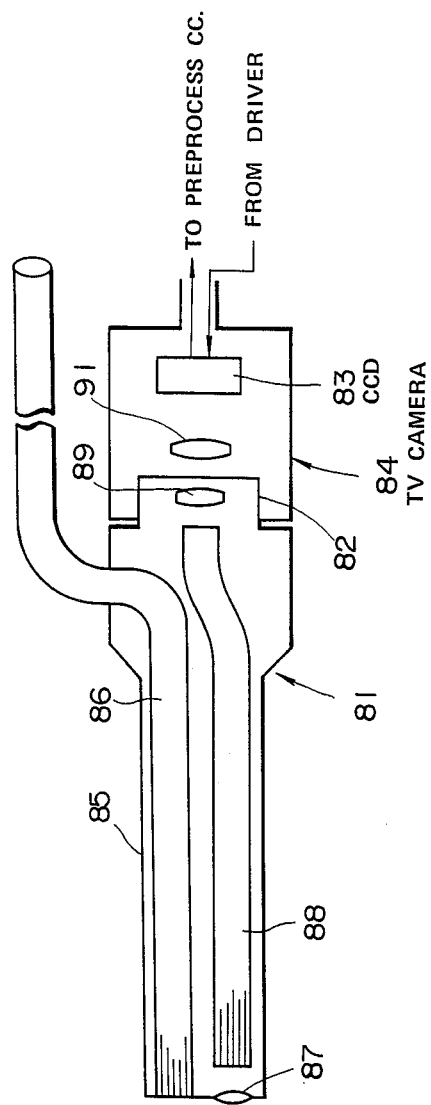
FIG. 9 shows another example of the structure of the electronic type endoscope.

The above-described first embodiment uses the electronic endoscope 12 as the imaging device. However, an endoscope with an external TV camera may also be used. An endoscope with the external TV camera includes an optical endoscope 81, and a TV camera 84, incorporating a CCD 83 is and mounted on an eyepiece portion 82 of the optical endoscope 81, as shown in FIG. 9.

The optical endoscope 81 has a flexible, elongated insertable portion 85. A light guide 86 is contained in the insertable portion 85. Illumination light is supplied when the incident end of the light guide 86 is mounted on the light source device 13. The image of an object illuminated by light emitted from the light emitting end of the light guide 86 is formed by an objective lens 87 on the incident side of a light guide 88, and is transferred to the light emitting end thereof at which the eyepiece 82 is provided. The transferred image can be observed in a magnified fashion through an eyepiece 89, and at the same time be formed through an image forming lens 91 on a CCD 83 incorporated in the TV camera 84. The video signal which has been photoelectrically converted by the CCD 83 is read out by the drive signal from the driver 25, and is input to the preprocessing circuit 26.

Thus, the optical endoscope 81 with the external TV camera 84 can be used in place of the electronic endoscope 12.

Light source devices for producing a light used by endoscopes to observe an object have been widely used in medical and industrial fields. These light source devices include a stroboscope for producing a light that flashes at a frequency that can be adjusted to coincide with any repeating high speed motion of an object so that the object can be observed as a still picture. In general, the stroboscope comprises a multistrobe lamp for supplying a light that illuminates an object in such a manner that the turning on and off of the lamp is switched over at a high speed. A lighting device lights the multistrobe lamp. A reference signal generating circuit generates a reference signal used to light the multistrobe lamp at a desired frequency. A synchronizing circuit supplies to the lighting device a signal synchronized with the motion of the object to be observed. The life of the multistrobe lamp is physically determined by the number of times the lamp is lit. In a known strobescope, the multistrobe lamp lights when the light source device is turned on and a lighting switch is turned on. Therefore, if the lighting switch is turned on, the lamp lights even when the endoscope needed to observe the object is not connected to the light source device. That is, the lamp lights even when the endoscope is not in operation, which shortens the life of the strobelamp.

Figure 10:
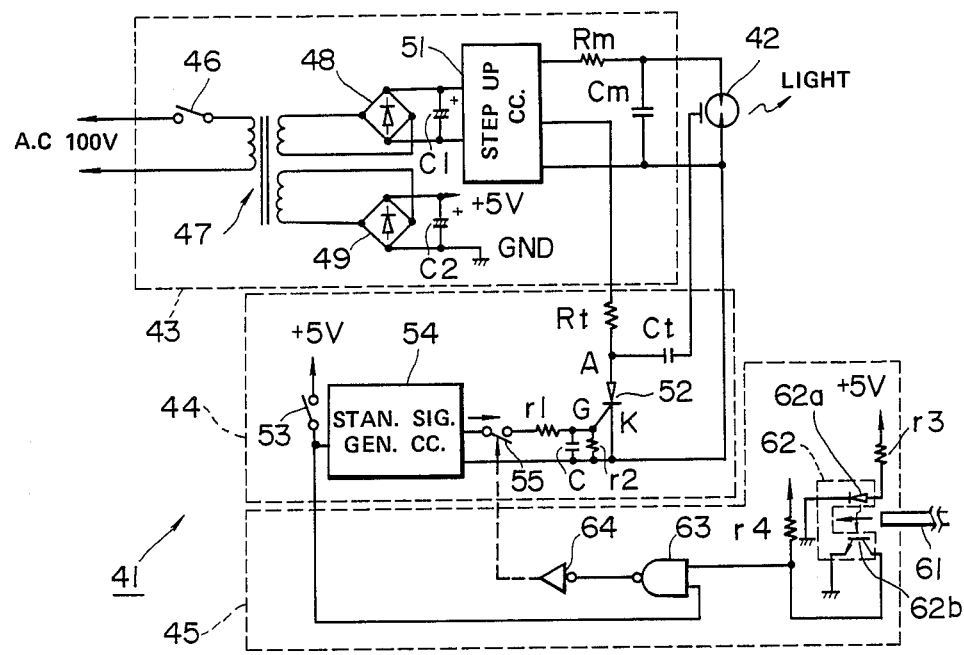
FIG. 10 is a circuit diagram of a light source device for a multistrobe lamp.

This problem may be eliminated by using a light source device shown in FIG. 10.

A light source device 41 shown in FIG. 10 includes a power source circuit 43 for supplying power to a multistrobe lamp 42, a trigger circuit 44 for supplying a light emitting timing signal for the multistrobe lamp 42, and a trigger control circuit 45 for determining whether or not a trigger signal is output from the trigger circuit 44.

The power source circuit 43 includes a power source transformer 47 having a power switch 46 at a primary winding. Full-wave rectifying circuits 48 and 49 are respectively connected to the two secondary windings of the power source transformer 47. Capacitors C1 and C2 are in turn respectively connected to the d.c. output terminals of the rectifiers. A step up circuit 51 comprising a DC—DC converter is connected to one of the dc output terminals so as to increase the voltage up to about 1000 V.

DC 5V is supplied as driving power from the other dc output terminal of the rectifiers to the trigger circuit 44 and the trigger control circuit 45.

The output terminal of the step up circuit 51 is connected to a main resistor Rm, which is in turn connected in series to the multistrobe lamp 42. A main capacitor Cm is also connected to output of the step up circuit 51 in parallel to the multistrobe lamp 42.

In the trigger circuit 44, about 300 V is applied from the step up circuit 51 to the anode A of a thyristor 52 through a trigger resistor Rt. The anode A is connected through a capacitor Ct to the light emission control trigger electrode of the multistrobe lamp 42. The cathode K of the thyristor 52 is connected to a GND.

Power is supplied to a standard signal generating circuit 54 through a lighting switch 53 used to light the multistrobe lamp 42. The light emitting timing signal outputting terminal of the standard signal generating circuit 54 is connected through an analog switch 55 and a resistor r1 to a gate G of the thyristor 52, which is in turn connected to the GND through parallel-connected combination of a resistor r2 and a capacitor c. Consequently, when the analog switch 55 is on, a trigger signal is applied to the gate G of the thyristor 52 by the light emitting timing signal which is output from the standard signal generating circuit 54 so as to light the multistrobe lamp 42.

Turning on and off of the analog switch 55 is controlled by the trigger control circuit 45.

In the trigger circuit 45, a photo interrupter 62 is provided at the recess that forms a light guide connector receiver for detachably receiving a light guide connector 61 provided on the forward end of the scope (universal cord). More specifically, the anode of a LED 62a is connected to a power supply of +5V through a resistor r3, while the cathode thereof is grounded. The LED 62a is kept lit while the power switch 46 is on. The LED 62a emits light toward the opposite side of the recess, and the emitted light is received by a photo transistor 62b which serves as a light receiving element. The emitter of the transistor 62b is grounded, and the collector thereof is connected to +5V through a resistor r4 as well as to one of the input terminals of a NAND gate 63. Consequently, when the light guide connector 61 is not mounted, the photo transistor 62b is on, and one of the input terminals of the NAND gate 63 is at a "L" level. The other input terminal of the NAND gate 63 is connected to the lighting switch 53. The output terminal of the NAND gate 63 is connected to the analog switch 55 through an inverter 64 so as to enable turning on and off of the analog switch 55 to be controlled by the output of the NAND gate 63.

The output of the NAND gate 63 is determined by whether or not the lighting switch 53 is on and by whether or not the light guide connector 61 for the scope is connected. More specifically, the output of the NAND gate 63 has a "L" level only when the scope is connected and the lighting switch 53 is on, and the analog switch 55 is thereby turned on through the inverter 64.

As a result, the multistrobe lamp 42 lights only when the lighting switch 53 is on and the scope is connected, as shown in the following table.

TABLE

| Lighting switch | OFF | ON | ON | OFF |
|---|---|---|---|---|
| Connection of scope | Not connected | Not connected | Connected | Connected |
| Lighting of multistrobe lamp | Not lighted | Not lighted | Lighted | Not lighted |

In the above-described arrangement, when the power switch 46 is turned on, power of AC 100 V is induced at the secondary winding of the power supply transformer 47, and the induced voltage is then converted into a dc voltage by the rectifying circuit 48 and the capacitor C1. Thereafter, the dc voltage is increased up to about DC 1000 V by the step up circuit 51, and the increased voltage passes through the main resistor Rm, and is charged in the main capacitor Cm. The energy charged in the main capacitor Cm is used to light the multistrobe lamp 42.

The rectifying circuit 49 and the capacitor C2 supply dc 5V to the trigger circuit 44 and the trigger control circuit 45.

Turning on of the analog switch 55 by the trigger control circuit 45 turns on the thyristor 52 by the light emitting timing signal of the standard signal generating circuit 54, by which trigger pulses are applied to the trigger electrode of the multistrobe lamp 42 so as to cause it to discharge (light). In other words, in FIG. 10, the multistrobe lamp 42 is caused to light in synchronism with a desired frequency by supplying the frequency to the thyristor 52 by the standard signal generating circuit 54. With the above-described arrangement, only when the scope is connected to the light emitting device 41 and the lighting switch 53 is on, the analog switch 55 can be turned on so as to light the multistrobe lamp 42. Therefore, lighting of the lamp 42 which occurs when the scope is not connected can be prevented, making it possible for the lamp 42 to be used effectively and increasing the life thereof. Since the lamp lights only when the scope is connected, the light of the light source device can be cut without provision of a light shielding means.

Figure 11:
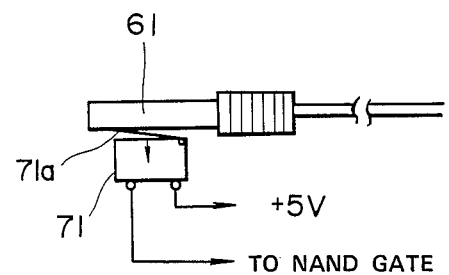
FIG. 11 is a side elevational view of another example of a scope connection detecting means.

The stroboscope shown in FIG. 10 uses a photo interrupter 62. However, a microswitch 71 shown in FIG. 11 may also be used in place of the photo interrupter 62. The example shown in FIG. 11 uses the microswitch 71 as a means for detecting the connection of the light guide connector 61. When the light guide connector 61 is connected to the connector receiver, as shown in FIG. 11, a lever 71a of the microswitch 71 is pressed, turning on the two contacts thereof. If one of the two contacts is connected to +5V while the other one is connected to one of the input terminals of the NAND gate 63, the same operation as in the case shown in FIG. 10 is ensured.

The color transmitting filter 35I for the rotary filter 23 and 23' is not limited to one which transmits one of the three primary colors, but it may be a filter which transmits a complementary color or one of the three colors containing white color.

If the solid state imaging device is of the interline transfer type which has an exclusively used transfer section, since the transfer is possible even during the exposure period after the charges have been transferred to the transfer section, the circumferential length of the light shielding portions 36a, 36b, and 36c can be further shortened, enabling the three color transmitting filters to be disposed with other different intervals.

The present invention can also be applied to an electronic type endoscope apparatus of the type which incorporates a hard endoscope employing a fiber scope or a relay optical system and a TV camera mounted on the eyepiece portion of the endoscope.

As will be understood from the foregoing description, the plurality of color transmitting filters are disposed in the circumferential direction with different intervals, and the light shielding portion caused by that disposal is used for eliminating of charges. Consequently, a color picture having a small color change is provided.

What is claimed is:

1. An electronic type apparatus comprising:
    an electronic type endoscope means including,
    an elongated insertable portion,
    light guide means for transferring an illumination light which has been supplied to an incident end thereof and for emitting said light from a light-emitting end thereof disposed at a forward end of said insertable portion,
    an objective lens system disposed at the forward end of said insertable portion for forming an image of an object, and
    a solid state image element for photoelectrically converting the image formed by said objective lens system;
    a field sequential type light source including, a lamp for emitting light with a wavelength in a visible range, a rotary color filter having a rotary frame on which a plurality of openings and a plurality of light shielding portions are provided in a circumferential direction, said plurality of light shielding portions including one light shielding portion which is longer in length than remaining light shielding portions, and a plurality of color transmitting filters which transmit a light with different wavelengths, said plurality of color transmitting filters being respectively mounted on said openings, and rotating means for driving said rotary color filter, said field sequential type light source to supply to said incident end of said light guide means illumination light which has passed through said color transmitting filters sequentially positioned in an optical path of a light by a drive of said rotating means;

a signal processing means including, a driver circuit for applying to said solid state imaging element a drive signal used to read out signals therefrom, and video signal processing means for processing signals which have been read out from said solid state imaging element by application of said drive signal to generate a predetermined video signal; and a color monitor for displaying said predetermined video signal which has been output from said video signal processing means.

2. An electronic type endoscope apparatus according to claim 1, wherein said drive circuit is to apply a drive signal to said solid state imaging element to read out signals therefrom and then output a sweep out signal used to eliminate dark current in the light shielding period, said longer light shielding portion is positioned in the optical path of the illumination light.

3. An electronic type endoscope apparatus according to either of claims 1 and 2, wherein said electronic type endoscope means comprises an electronic scope in which said solid state imaging element is disposed in a focal plane of said objective lens system.

4. An electronic type endoscope apparatus according to either of claims 1 and 2, wherein said electronic type endoscope means comprises an optical endoscope having an image guide means for transferring the image formed by said objective lens system, and a TV camera mounted on an eyepiece portion of said optical endoscope, said TV camera incorporating said solid state imaging element for photoelectrically converting the image which has been transferred by said image guide means.

5. An electronic type endoscope apparatus according to either of claims 1 and 2, wherein said rotating means rotates said rotary color filter with a period which is equal to one frame period of said predetermined video signal.

6. An electronic type endoscope apparatus according to claim 5, wherein said rotation period is 1/25s.

7. An electronic type endoscope apparatus according to either of claims 1 and 2, wherein said longer light shielding portion is made longer in the circumferential direction than other light shielding portions by a value corresponding to about 60 degrees.

8. An electronic type endoscope apparatus according to either of claims 1 and 2, wherein said video signal processing means generates a video signal for use in a PAL system.

9. An electronic type endoscope apparatus according to either of claims 1 and 2, wherein said color monitor is of the type which uses a PAL system.

10. An electronic type endoscope apparatus according to claim 8, wherein said video signal processing means has an A/D converter for A/D converting signals which have been read out from said solid state imaging element, a memory for temporarily storing A/D converted digital signals, a D/A converter for D/A converting signals which have been read out from said memory, and a postprocessing circuit for converting D/A converted analog signals into a predetermined video signal.

11. An electronic type endoscope apparatus according to claim 10, wherein said postprocessing circuit generates a video signal for use in a PAL system.

12. An electronic type endoscope apparatus according to claim 11, wherein said postprocessing circuit generates a video signal for use in an NTSC system.

13. An electronic type endoscope apparatus according to either of claims 1 and 2, wherein a light shielding piece that blocks part of said opening can be mounted on more than two of said plurality of openings formed in said rotary frame, and a length of said opening can be adjusted by said light shielding piece.

14. An electronic type endoscope apparatus according to either of claims 1 and 2, wherein said rotary color filter may be a second rotary color filter having a second rotary frame on which a plurality of openings and a plurality of light shielding portions are formed equiangularly in the circumferential direction, and a plurality of color transmitting filters respectively mounted on said second openings, said color transmitting filters transmitting a light having different wavelengths.

15. An electronic type endoscope apparatus according to claim 14, wherein said second rotary color filter is rotated with a period of 1/30s.

16. An electronic type endoscope apparatus according to claim 8, wherein said rotary color filter is rotated with a period which is equal to one frame period of said video signal for use in a PAL system, i.e., 1/25s.

17. An electronic type endoscope apparatus according to claim 14, wherein the illumination period of the light which has passed through said color transmitting filters of said rotary color filter is made equal to that of the light which has passed through said color transmitting filters of said second rotary color filter.

* * * * *